United States Patent [19]

Hecker et al.

[11] Patent Number: 4,716,179

[45] Date of Patent: Dec. 29, 1987

[54] USE OF NON-IRRITATING OR SLIGHTLY IRRITATING AND/OR PROMOTING DITERPENE ALCOHOL AND OF DERIVATIVES THEREOF AS ANTINEOPLASTIC PREPARATIONS

[75] Inventors: Erich Hecker, Heidelberg-Handschuhsheim; Hans Osswald; Rainer Schmidt, both of Heidelberg, all of Fed. Rep. of Germany

[73] Assignee: Stiftung Deutches Krebsforschungszentrum, Heidelberg, Fed. Rep. of Germany

[21] Appl. No.: 584,738

[22] Filed: Feb. 29, 1984

Related U.S. Application Data

[63] Continuation-in-part of Ser. No. 113,760, Jan. 21, 1980, abandoned.

[30] Foreign Application Priority Data

Jan. 23, 1979 [DE] Fed. Rep. of Germany ....... 2902506

[51] Int. Cl.$^4$ .............................................. A61K 31/12
[52] U.S. Cl. ..................................................... 514/691
[58] Field of Search ......................................... 514/691

[56] References Cited

PUBLICATIONS

Chemical Abstracts 84:100631j (1976).
Armuth et al., Z. Krebsfousch 85 pp. 79–82 (1976).

*Primary Examiner*—Jerome D. Goldberg
*Attorney, Agent, or Firm*—Robbins & Laramie

[57] ABSTRACT

The present invention is directed to a method of inhibiting the growth of cancer cells in a lower animal host through the use of phorbol.

8 Claims, No Drawings

USE OF NON-IRRITATING OR SLIGHTLY IRRITATING AND/OR PROMOTING DITERPENE ALCOHOL AND OF DERIVATIVES THEREOF AS ANTINEOPLASTIC PREPARATIONS

This is a continuation-in-part of Ser. No. 113,760, filed Jan. 21, 1980, now abandoned.

The invention concerns new antineoplastic preparations, as well as a process for the preparation of their active components.

For therapeutic application are used antineoplastic preparations which are characterized in that they contain as an active antineoplastic component non- or slightly irritating and/or non- or slightly irritating and-/or non- or slightly promoting diterpene alcohol, phorbol.

The term non- or a slightly irritating and/or non- or slightly promoting means an irritating effectiveness of <1% of the irritating action of the 12-O-tetradecanoyl-phorbol-13-acetate (TPA). In order to simplify the expression, we will speak hereafter only of non-irritating and/or non-promoting, which will also comprise, however, the slightly irritating and/or slightly promoting compounds of the above definition. The term "irritating" and "non-irritating" is well defined. This property is tested in the standardized test on the mouse ear. The term "promoting" or "non-promoting" has likewise been well defined in the meantime. This property is tested in the standardized promotion test on the back skin of the mouse.

The chemical structure of the irritating principles has been known only since 1966, when it was possible to isolate and prepare these principles in pure condition to clarify their structure, and to characterize their biological action on skin-irritating seed oil of the Euphoriaceae Croton tiglium (croton oil), since 1968 in numerous other Euphorbiaceae and later also in Thymelaeaceae (3–5). These are esters of tri- and tetracylic polyfunctional diterpenes, which were unknown up to that time, whose structures can be traced back to the hypothetical tri- or tetracyclic diterpene hydrocarbons Daphnane (1), Tigliaene (2) and Ingenane (3) (see Example 2). In addition, esters of macrocyclic, polyfunctional diterpenes were isolated from Euphoriaceae, whose structures can be derived from the hypothetical macrocyclic diterpene-hydrocarbon Lathyrane (4).

Unlike the esters derived from 1–3, hence Daphnane, Tigliane and Ingenane, the macrocylic esters or Lathyrane or of the diterpenes derived therefrom suggests that it is closely related to the biogenesis of the irritating principles of the above plant families. (6).

The invention thus concerns substantially the use of the non- or slightly irritating and/or non- or slightly promoting diterpene alcohol, phorbol.

Many though not all of the presently known irritating diterpene esters of the Daphnane-, Tigliane- and Ingenane type also have a carcenogenic or qualified cancer-inducing effect (3–5). They were characterized in the initiation-promotion-progression model of the carcinogenesis of the mouse skin as tumor promotors, and show in independent tests neither mutagenic (4/5) nor alkalizing action (7). Today they are considered the prototype of carcinogens with an initiation- (or tumor promoting) action (3,4,8). In the ethiology of human tumors they can play the role of cancer risk factors of the second order (3,4), compared to solitary carcinogens. The term "promoting" or "non-promoting" has likewise been well defined in the meantime. This property is tested in the standardized promotion test on the back skin of the mouse.

Typical examples of irritating and/or promoting diterpene esters are the structures of 9,13,14-ortho-tetradecanoyl resiniferonal (1a), 13-O-tetradecanoyl-12-dosoxyphorbol (2a) and 3-O-hexadecanoylingenol (3a) shown in Example 2. They contain relatively few oxygen functions and are representative of the wide spectrum of irritating and more or less promoting polyfunctional diterpene esters.

Since it had already been shown (3,4) that the irritating action is not necessarily linked with the promoting action, it was now tested whether the irritating properties of the diterpene esters are in casual relation to their antineoplastic action. For the tests, which are compiled in enclosure 4, records 1 and 2, were used the irritating and promoting (3,4) diterpene esters Simplexin (1d), TPA (2c), as well as ingenol-3,20-dibenzoate (3c) and the irritating, but not promoting (2,3) diterpene ester resiniferatoxin (1c). As a corresponding non-irritating (3,4) polyfunctional diterpene alcohol was used phorbol (2d) (for all structures see Example 2). As a tumor model was used sarcoma 180 and the Ehrlich-carcinoma. In the latter, Endoxan (cyclophosphamide) serves as a positive control.

The tests with the solid sarcoma 180 (Example 3, record 1) showed that both the more or less irritating and promoting diterpene esters TPA, Simplexin and ingenol-3,20-dibenzoate, and the non-irritating and—as it will be explained below; slightly promoting phorbol lead to tumor inhibitions of more than 50%. Just as in the solid hyperdiploid Ehrlich carcinoma, a lower dose than 20% of the DL 50 was partly used. In the latter tests, the irritating and/or carcinogenic diterpene esters, as shown in record 2, series 3, 4 and 6, were given twice a week, because the Ehrlich carcinoma can be less influenced by tumor inhibitors than sarcoma 180 used in record 1. It was found that TPA (series 3) as well as resiniferatoxin (series 6) had neither a curative nor a significant tumor-inhibiting effect (50%) in these carcinomas. Endoxan used assa positive control for series 2 showed the best results with regard to tumor inhibition and curing rate (5 out of 10 animals cured).

In all test groups treated with the irritating and/or promoting esters TPA, Simplexin, ingeol-3,20-dibenzoate and resiniferatoxin, severe dermatifides could only be prevented by changing the subcutaneous point of application. Despite these measures, inflammable hardened spots (indurations) were observed at the point of injection which lasted for about 8 days. But no changes were found at the point of injection in the subcutaneous application of phorbol. A narrow therapeutic range of the irritating and/or promoting diterpene esters was thus found, which can be shown particularly in the example of Simplexin (record 2, series 4). Though a more than 50% tumor inhibition could be achieved with Simplexin in a dose of 2×2 mg/kg per week (record 2, series 4), and two animals were cured, (a cure in all the above tests means that complete tumor remission up to at least 90 days after the end of the test), three deaths occurred in this series in the third week because of toxic effects of Simplexin.

Simplexin represents, however, the type of structure that shows partly a high antileukemic effect according to the results of recent tests (3,4) and according to results by Kupchan et al.

Unlike the irritating and/or promoting diterpene esters, however, phorbol was tolerated better. Three oral or subcutaneous applications of 40 mg/kg phorbol each (record 2, series 7,8), hence a total dose of 120 mg/kg phorbol per week, have about the same effect as two subcutaneous or intravenous applications per week in a total dose of 80 mg/kg phorbol according to series 9 and 10 of the same record. The oral administration of phorbol (series 7), despite two cured animals, shows no significant tumor inhibition in the other animals, while in the other series (8-9), in addition to two or three cured animals a tumor inhibition of more than 50% was observed.

This shows for the first time that the non-irritating and non-promoting diterpene alcohol phorbol has a surprisingly pronounced antineoplastic effect, and has definite advantages over the irritating and/or promoting diterpene esters, since the irritating esters lead in subcutaneous application to induration of the point of injection and can not be applied repeatedly either orally or intravenously, because they are highly toxic.

The effect of diterpene alcohol on the intramuscularly implanted Retothel sarcoma was compared in subcutaneous application with the action of Endoxan. Only one dose was used, while Endoxan was tested with two doses.

In the dosage used, all tested diterpene alcohols showed clear tumor inhibition comparable to Endoxan. This is in contrast to the view that the inhibition of the tumor is due to the irritating action of the diterpene derivatives. In this connection it should be pointed out that contradictory studies have been published (14) on the leukemogenic effect of phorbol (10-13) that alpha-phorbol does not seem to be leukemogenic (15) and that phorbol, 4 alpha-phorbol and 12-desoxyphorbol have a slightly promoting effect (11,13,15,16,17).

Example 5 shows the testing of the following substances in leukemia P 388:

1. The polycyclic diterpene alcohols 12-desoxyphorbol (2b), phorbol (2d) and 4-alpha-phorbol (2f) as reference substances, which had already been tested in other tumor models.

Because it is known from experience that Endoxan (cyclophosphamide) works better in a single dose in this type of leukemia (Example 5, series 2,3) than in two doses in an interval of 1 week, a different dosing pattern was partly used in subcutaneous administration.

With regard to the curing rate and the ILS (percentual increase of survival in the test series, compared to the control series), phorbol proved in a single dose of 100 mg/kg comparable to the best chemotherapeutic results with Endoxan (series 3,4).

These results in leukemia 388 thus verify that non-irritating polyfunctional diterpene alcohols, particularly phorbol, of the structural types 1-4 have a pronounced antineoplastic effect.

The optimum dose of the diterpene derivatives depends on the respective pharmacokinetics of the substance and must be determined in the specific case, which is readily possible by series tests.

In general it can be said that phorbol is a suitable antineoplastic agent and seems to involve not only a lesser risk compared to alkylating agents, as far as "iatrogenic carcinogenesis" is concerned but also permits more selective damages to tumor cells, in addition to normal cells. Because of the few side effects of this compound, the new active principle should bring a substantial improvement in the chemotherapy of cancer.

Summarizing, the following polyfunctional diterpene is mentioned particularly for the therapy of tumors:

1. Phorbol

As a typical example for the preparation of tri- and tetracyclic polyfunctional diterpenes from vegetable material, the preparation of the tigliane derivative phorbol from the seed oil of croton tiglium L (croton oil) will be described below.

2. Forms of drugs

The forms of drugs used depend usually on the intended type of application and on the amount of the single dose to be selected. It should be kept in mind that the claimed phorbol must be principally considered unstable (e.g. to oxygen, acids, alkali and light). It is therefore advisable to keep the antineoplastic component in all forms of drugs in solid form in the freezer (drug form: tablet or capsule; for drugs to be injected parenterally, as a dry substance in ampules). For parenteral application, the solution or suspension must be prepared fresh. A list is contained in Table 3, Example 7, which is based on W. A. Ritschel, Angewandte Biopharmazie, Wiss. Verlagsgesellschaft Stuttgart, 1973.

The following describe the preparation of phorbol.

Preparation of the tetracyclic polyfunctional diterpene phorbol from croton oil 500 g croton oil, obtained in known manner from the seed of Croton tiglium L., are shaken with a solution of 55 g $Ba(OH)_2.8 H_2O$ in 2.25 l methanol for 10 to 12 hours under nitrogen. After filtration from the precipitated barium soaps, the filtrate is concentrated in the rotary evaporator at 40 deg. C. bath temperature until no methanol passes over anymore. The oily residue is taken up with 2 l water, and the mixture is extracted twice with 500 ml ether each. The remaining water phase (in which the phorbol is contained) is standardized with 2N-sulfuric acid to a pH 5. After adding 40 ml saturated sodium sulfate solution, the mixture is stored for 12 hours at 4 deg. C. The precipitated barium sulfate is then removed by suction, the solution standardized with 2N soda lye to pH 7.0, and extracted successively with 500 ml each acetic ethyl ester and ether. The aqeuous phase is concentrated in the rotary evaporator at 45 deg. C. until no water passes over any more. To the viscous residue are added 100 ml ethanol and the precipitated sodium sulfate is filtered off. The sodium-sulfate residue is extracted with warm ethanol so often until a sample shows no (or only a very weak) red coloration on boiling with 1 ml conc. hydrochloric acid ("phorbol reaction"). The combined filtrates are concentrated to 50 to 60 ml, and the viscous solution is stored at 4 deg. C. Phorbol crystallized mostly spontaneously from this preparation; if this is not the case, the solution may be too viscous and must then be diluted with some ethanol. After 4 weeks the crystals are removed by suction, spread on earthenware slabs and stored for several days at 4 deg. C. under nitrogen. This way we obtain 5.5 to 6.1 g pure white phorbol-$C_2H_5OH$ ("alcohol phorbol"). The solvate is unstable and is converted to phorbol ("water phorbol"). To this end 5.8 g phorbol $C_2H_5OH$, e.g. are dissolved in 100 ml water at 60 deg. C. The solution is concentrated in the rotary evaporator at 60 deg. C, until crystals are separated. This preparation is kept for 1 week at 4 deg. C. under nitrogen, and then the separated crystals are removed by suction (e.g. 4.4 g phorbol, mp. 250-1 deg. C., decom.)

Preparation of the macrocyclic polyfunctional diterpene 6,17-epoxylathyrol from end oil of Euphorbia lathyris L.

The oil is obtained by extraction of the seed of E. lathyris L., grinding in a meat grinder with peroxide-free diethyl ether, and subsequent withdrawal of the solvent in the rotary evaporator. After prolonged standing of the seed oil at 4 deg. C., the colorless 6,17-epoxylathyrol-3-phenylacetate-5,15-diacetate crystallizes therefrom, which is recrystallized from hot ethanol. Melting point 199-200 deg. C.

2 g 6,17-epoxylathyrol-3-phenylacetate-5,15-diacetate are dissolved in 80 ml methanol and mixed with 100 ml 0.5 n methanolic potash lye. After stirring for 3 hours under nitrogen at room temperature, the reaction is stopped with 6 ml acetic acid, the solution is concentrated in the rotary evaporator, the residue mixed with methylene chloride and removed by suction from the precipitated potassium acetate. The reaction product is dissolved in 150 ml methylene chloride and extracted three times with 100 ml 2n soda solution each to remove the released phenylacetic acid. The residue is washed alkali-free with some water, dried over magnesium sulfate, and after suction and concentration we obtain 1150 mg 6,17-epoxylathyrol (90% yield). After triple receystallization from ethanol/water and drying in the high vacuum, we obtain the macrocylic polyfunctional diterpene with a melting point of 204-207 deg. C.

EXAMPLE 1

References

1. J. L. Hartwell, Plants used against Cancer. A. Survey. Lloydia 32, 153-205 (1969); 34, 250-252 (1971).
2. E. Hecker and R. Schmidt, Phorbolesters—the Irritants and Cocarcinogens of Croton tiglium L., Progr. Chem. Org. Nat. Products 31, 375-467 (1974); E. Hecker, Isolation and Characterization of the Cocarcinogenic Principles from Croton Oil in Methods in Cancer Research Vol. VI. edit. by H. Busch, p. 439-484, 1971, Academic Press, New York-London.
3. Hecker, New Toxic, Irritants and Cocarcinogenic Diterpene Esters from Euphorbiaceae and from Thymelaeaceae, Pure appl. Chem. 49, 1423-1431 (1977).
4. E. Hecker, Structure-Activity Relationships in Diterpene Esters Irritant and Cocarcinogenic to Mouse Skin, in Carcinogenesis, Vol. 2, Mechanisms of Tumor Promotion and Cocarcinogenesis, edit. by T. J. Slaga, A. Sivak and R. K. Boutwell, Raven Press, New York, 1978, pp. 11-48
5. F. J. Evans and C. J. Soper, The Tigliane, Daphnane and Ingenane Diterpenes, Their Chemistry, Distribution and Biological Activities, Lloydia 41, 193-233 (1978).
6. W. Adolf and E. Hecker, Diterpenoid Irritants and Cocarcinogens in Euphorbiaceae and Thymelaecceae: Structural Relationships in view of their Biogenesis, Israel J. Chem. 16, 75-83 (1977).
7. E. Hecker et al. unpublished.
8. E. Hecker, Topical problems of carcinogenesis. Z. Krebsforschung, 78, 99-112 (1972).
9. E. Hecker and A. Schroedersecker: Tests 1970/71, not yet published for reasons of patent law.
10. I. Berenblum and V. Lonai, The leukemogenic action of phorbol, Cancer Res. 30, 2744-2748 (1970).
11. V. Armuth and I. Berenblum, Systemic promoting action of phorbol in liver and lung carcinogenesis in AKR mice, Cancer Res. 32, 2259-2262 (1972).
12. V. Armuth, Leukemogenic action of phorbol in intact and thymectomized mice of different strains, Brit. J. Cancer 34, 616-522 (1976).
13. V. Armuth and I. Berenblum, Promotion of mammary carcinogenesis and leukemogenic action by phorbol in virgin female Wistar rats, Cancer Res. 30, 2744-2748 (1970).
14. D. Gericke, W. Kovac and E. Hecker, On a possible cocarcinogenic and immunosuppressive Activity of Phorbol in AKR-Mice, Z. Krebsforsch. 82, 183-189 (1974).
15. V. Armuth, I. Berenblum, R. Schmidt and E. Hecker in preparation.
16. M. W. Baird and R. K. Boutwell, Tumor-promoting activity of phorbol and four diesters of phorbol in mouse skin. Cancer Res. 31, 1074-1079 (1971).
17. V. Armuth and I. Berenblum, Phorbol as a possible systemic promoting agent for skin carcinogenesis. Z. Krebsforsch. 85, 79-82 (1976).
18. S. M. Kupchan, C. W. Sigel, M. J. Matz, J. A. S. Renauld, R. C. Haltiwanter and R. F. Bryan, Jatrophone, a Novel Macrocylic Diterpenoid Tumor Inhibitor from Hatropha gossypifolia, J. Amer. Chem. Soc. 92, 4476 (1970).
19. S. M. Eupchan, C. W. Sigel, M. J. Matz, C. J. Gilmore and R. F. Bryan, Structure and Stereochemistry of Jatrophone, A Novel Macrocylic Diterpenoid Tumor Inhibitor, J. Amer. Chem. Soc. 98, 2295 (1976).
20. H. Lotter, H. J. Opferkuch and E. Hecker, Tetrahedron Letters, in press.

EXAMPLE 2

The hypothetical polycyclic diterpenes 1-4 and typical diterpene derivatives which were isolated from Euphorbiaceae and Thymelaceae.

Daphane (1)

1a—9,13,14-ortho-tetradecanoyl resiniferonol: $R^1$=alkyl, $R^2$=H.

1b—resiniferonol

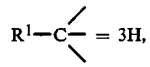

$R^2$=H.

1c—resiniferatoxin: $R^1$=$CH_2C_6H_5$, $R^2$=$COCH_2C_6H_3$ (OH, $OCH_3$).

1d—Simplexin: 5 beta-hydroxy-6,7a-epoxy-resiniferonol-9,13,14-ortho-decanic ester.

Tigliane (2)

2a—13-O-tetradecanoyl-12-desoxyphorbol: $R'$=H, $R^I$=tetradecanoyl, $R^2$=H.

2b—12-desoxyphorbol: $R'$=H, $R^1$=$R^2$=H.

2c—12-O-tetradecanoyl phorbol-13, acetate (TPA): $R'$=tetradecanoyloxy, $R^1$=$COCH_3$, $R^2$=H.

2d—phorbol: $R'$=OH, $R^1$=H, $R^2$=H or 12,13,20-triacetate, $R'$=$OCOCH_3$, $R^1$=$R^2COCH_3$.

2e—cryptic TPA: $R'$=tetradecanoyloxy, $R^1$=$COCH_3$, $R^2$=acyl.

2f—4-alpha-phorbol: 2d corresponding to 2d with 4-alpha-tigliane structure.

Ingenane (3)
3a—3-hexadecanoylingenanol: $R^1$=hexadecanoyl, $R^2$=H.
3b—ingenol: $R^1=R^2$=H.
3c—ingenol-3,20-dibenzoate: $R^1=R^2=COC_6H_5$.
3d—cryptic 3-hexadecanoylingenol: $R^1$=hexadecanoyl, $R^2$=acyl.
3e—16-hydroxyingenol: see 3b.

Lathyrane (4)
4a—diterpene exter: "$L_3$": $R^1=R^2=COCH_3=COC_6H_5$.
4b—ingol-12-acetate: with 4 beta-lathyrane structure
4c—lathyrol: $R^1=R^2=R^3$=H.
4d—16,17-epoxylathyrol-3-phenylacetate-5,15-diacetate.

| EXAMPLE 3 record 1. | | | | | | | |
|---|---|---|---|---|---|---|---|
| Assistant: Bollow | | | | date of transplant: 1/14/77 | | | |
| Strain: Swiss | | | | state of therapy: 1/17/77 | | | |
| Tumor: sarcoma 180 | | | | days of treatment: once a week | | | |
| Mode of transplant: i.m. | | | | duration of therapy: 3 weeks | | | |
| Weight of tumor at start of treatment: 1.2 φgram | | | | end of test: 2/4/77 | | | |
| | | | | no. of animals/series 15 | | | |
| No. of series | Preparation | Single dose mg/kg | Total dose mg/kg | cured | Died | Weight of tumor | Body weight difference |
| 1 | Negative control | — | — | — | — | 12.20 1.52 | −20.02% |
| 2 | TPA sc. | 0.5 | 1.5 | — | — | 5.12 0.68 | −3.13% |
| 3 | Phorbol sc. | 20 | 60 | — | — | 5.10 1.69 | −0.38% |
| 4 | Simplexin sc. | 2 | 6 | — | — | 5.12 1.40 | −4.43% |
| 5 | Ingenol-3,20-dibenzoate, sc. | 5 | 15 | — | — | 5.72 1.70 | −3.42% |

Note concerning group 4:
Massive dermatitides were observed in all mice, with complete loss of hair. The underlying skin surface was hard and brittle.

| EXAMPLE 3 record 2 | | | | | | | |
|---|---|---|---|---|---|---|---|
| Assistant: Bollow | | | | date of transplant: 2/11/77 | | | |
| Strain: Swiss | | | | Start of therapy: 2/14/77 | | | |
| Tumor: Ehrlich-diploid | | | | Duration of therapy: 3 weeks | | | |
| Mode of transplant: i.m. | | | | End of test: 3/7/77 | | | |
| Weight of tumor at start of treatment: 1.0 g φ | | | | No. of animals/series 15 | | | |
| No. of series | Preparation | Single dose mg/kg | Total dose mg/kg | Cured | Died | Weight of tumor | Body weight difference |
| 1 | Negative control | — | — | — | — | +10.20 −1.27 | −11.25% |
| 2 | Positive Control Endoxan sc. 1 × week | 90 | 270 | 5/15 | — | +3.35 −1.00 | −6.53% |
| 3 | TPA sc. Mo. + Thu | 0.5 | 3.0 | — | — | +5.39 −1.75 | −2.32% |
| 4 | Simplexin sc. Mo + Thu | 2 | 12 | 2/15 | 3/15 | +4.15/12 −2.20/12 | — |
| 5 | Ingenol-3,20 dibenzoate, sc. Mo + Thu | 2.5 | 15.0 | — | — | +4.41 −1.37 | −3.44% |
| 6 | Resinifera toxin sc. Mo + Thu | 0.1 | 0.6 | — | — | +6.22 −2.66 | −4.55% |
| 7 | Phorbol oral Mo + Wed + Fri | 40 | 350 | 2/15 | — | +6.00 −3.40 | −4.12% |
| 8 | Phorbol sc. Mo, Wed + Fri | | | | | +5.05 −3.52 | −3.98% |
| 9 | Phorbol sc. Mo + Thu | 40 | 240 | 2/15 | — | +4.30 −1.89 | −2.95% |
| 10 | Phorbol i.v. Mo. + Thu | 40 | 240 | 3/15 | — | +4.90 −2.61 | −1.10% |

| EXAMPLE 4 | |
|---|---|
| Assistant: Merkel | Date of transplant: 4/25/77 |
| Test no. 13/1–19 | Start of therapy: 4/28/77 |
| Strain: Swiss | Days of treatment: 7 |

-continued
EXAMPLE 4

Tumor: Rethothel sarcoma  
Mode of transplant: i.m.  
Weight of tumor at start of treatment: ab 1.5 g  
Duration of therayp: 4 weeks  
End of test: 5/24/77  
No. of animals/series 15

| No. of | Preparation | Single dose mg/kg | Total dose mg/kg | Cured | Died | Weight of tumor | Body weight difference |
|---|---|---|---|---|---|---|---|
| 1 | Negative control | — | — | — | — | 10.5 | 33.2 |
|   |   |   |   |   |   | 2.0 | −11.7% |
| 2 | Positive control | 60 | 240 | — | — | 4.1 | 31.0 |
|   |   |   |   |   |   | 1.1 | −3.8% |
| 3 | Endoxan sc. | 90 | 350 | — | — | 2.9 | 31.8 |
|   |   |   |   |   |   | 1.1 | −2.5% |
| 4 | 4 alpha-phorbol sc. repeated after 72 h | 80 | 400 | — | — | 3.7 | 33.8 |
|   |   |   |   |   |   | 2.5 | +2.6% |
| 5 | Phorbol sc. repeated after 72 h | 80 | 480 | — | — | 2.5 | 30.6 |
|   |   |   |   |   |   | 1.0 | +5.8% |
| 6 | 16-hydroxyingenol sc. repeated after 72 h | 80 | 560 | — | — | 2.5 | 31.9 |
|   |   |   |   |   |   |   | +5.0% |

Note to groups 4 and 5:  
Due to lack of substance, treatment was no longer continued in test no. 4 in the last week and in test no. 5 the last injection was foregone in the last week.

Examples  
Assistant: You/De.  
Test no. 4/78  
Strain: $D_2B_6F_1$  
Tumor P 388  
Mode of transplant: ip.  
Weight of tumor at start of treatment: -

Date of transplant: 2/27/78  
Start of therapy: 2/28/78  
Days of treatment: 1 + 4 × week  
Duration of therapy: 1 week  
End of test 4/17/78  
No. of animal series 15

| No. of series | Preparation | Single dose mg/kg | Total dose mg/kg | Cured | Died | ILS % | Survival time median |
|---|---|---|---|---|---|---|---|
| 1 | Negative Control | — | — | — | 15/15 | — | $10 - \frac{14.00-}{15}$ |
| 2 | Positive | 40 | 40 | 7/15 | 8/15 | 90.93 | $16 - \frac{23.37-}{42}$ |
| 3 | control | 30 | 30 | 9/15 | 6/15 | 101.42 |  |
| 4 | Endoxan sc. | 120 | 120 | 11/15 | 4/15 | 91.90 | $14 - \frac{18.25-}{29}$ |
| 5 | Phorbol sc. | 100 | 100 | 12/15 | 3/15 | 95.35 | $14 - \frac{17.66-}{21}$ |
| 8 | Phorbol sc. on four days | 4 × 100 | 400 | 9/15 | 6/15 | 85.71 | $12 - \frac{20.00-}{51}$ |

TABLE 1
EXAMPLE 6
Polyfunctional polycyclic diterpenes of the tigliane type from Euphorbiaceae and Thymelaeaceae.

| Basic alcohol | Oxygenation | Plant | Ref. No. * |
|---|---|---|---|
| 4-Deoxyphorbol | $O_5$ | Euphorbia tirucalli L. | 30 |
| 12-Deoxyphorbol |  | E. triangularis Desf. | 39 |
|  |  | E. resinfiera Berg.[a] | 58 |
|  |  | Pimelea prostrata Willd. | 125 |
| Phorbol | $O_6$ | C. tiglium L. | 49 |
|  |  | C. sparsiflorus Morong | 119 |
|  |  | C. oblongifolius Roxb. | 36 |
|  |  | E. tirucalli L.[b] | 30,31 |
|  |  | Sapium japonicum Pax and Hoffm. | 82 |
| 4-Desoxy-16-hydroxyphorbol |  | C. flavens L. | 55,120a |
| 12-Desoxy-16-hydroxyphorbol |  | E. cooperi N.E. Brown[b] | 38 |
| 16-Hydroxyphorbol | $O_7$ | Aleurites fordii Hemsl. | 84 |
|  |  | C. flavens L. | 55,120a |
| 12-Desoxy-5beta-hydroxyphorbol- |  | Hippomane mancinella L. | 2 |
|  |  | Pimelea prostrata Willd. | 18 |

TABLE 1-continued
EXAMPLE 6
Polyfunctional polycyclic diterpenes of the tigliane type from Euphorbiaceae and Thymelaeaceae.

| Basic alcohol | Oxygenation | Plant | Ref. No. * |
|---|---|---|---|
| 6alpha,7alpha-oxide |  |  |  |

[a] and many other euphorbia species (see 25)  
[b] and some other euphorbia species (see 25)  
*all figures in this column and in footnotes a and b refer to the references contained in EXAMPLE 1.

TABLE 2
EXAMPLE 7
Forms of drugs for active antineoplastic components based on the claimed polyfunctional diterpenes or -derivatives.

| Type of application/administration |  | Form of drug |
|---|---|---|
| peroral | p.o. | Tablet[a] capsule[a] |
| parenteral | i.v. | hydrophilic solution[b] |
|  | i.m. | hydrophilic solution[c] or suspension |

TABLE 2-continued

EXAMPLE 7

Forms of drugs for active antineoplastic components based on the claimed polyfunctional diterpenes or -derivatives.

| Type of application/administration | Form of drug |
|---|---|
| i.m. | oily solution or suspension[d] |

[a] With conventional aids (see Ritschel, table 23.3, p. 430) gastric juice-resistant by coating with film-forming materials (protection of the active substances against possible changes by the highly acid medium of the gastric juice). For examples see Ritschel, table 22.4, p. 401.

[b] As solvents can be used polyethylene glycol and ethanol, as solubilizing agents Cremophor EL[R]; see Ritschel, table 24.9, p. 448, as well as table 24.6, p. 446 and table 24.8, p. 447.

[c] As a solvent is used, e.g. polyethylene glycol

[d] As a vehicle is used, e.g. sesame oil, isopropyl myristate etc. See Ritschel, table 25.2, p. 463 and p. 461 ff.

We claim:

1. The method of treating transplanted tumor-afflicted animal subjects which comprises administering to said subjects an anti-transplanted tumor effective amount of phorbol, said phorbol being incorporated in a carrier material.

2. The method of claim 1, wherrein said carrier material is selected from the group consisting of polyethylene glycol, ethanol, sesame oil, cremophor and isopropyl myristate.

3. The method of treating transplanted tumor-afflicted animal subjects, which comprises administering to said subjects phorbol in a weekly dose lower than 20% of the DL 50, said phorbol being incorporated in a carrier material.

4. The method of claim 3, wherein said carrier material is selected from the group consisting of polyethylene glycol, ethanol, sesame oil, Cremophor and isopropyl myristate.

5. A method for inhibiting the growth of cancer cells in a lower animal host which comprises the administration to the host of a cancer cell growth-inhibiting effective amount of a pharmaceutical composition which comprises phorbol and a pharmaceutically acceptable carrier.

6. The method of claim 5 wherein said carrier is selected from the group consisting of polyethylene glycol, ethanol, sesame oil, cremophor and isopropyl myristate.

7. The method of claim 5 wherein a weekly dose of phorbol lower than 20% of the DL 50 is administered.

8. The method of claim 6 wherein a weekly dose of phorbol lower than 20% of the DL 50 is aministered.

* * * * *